United States Patent
Lee et al.

(10) Patent No.: US 12,156,719 B2
(45) Date of Patent: *Dec. 3, 2024

(54) APPARATUS AND METHOD FOR ESTIMATING BODY TEMPERATURE

(71) Applicant: SAMSUNG ELECTRONICS CO., LTD., Suwon-si (KR)

(72) Inventors: So Young Lee, Daejeon (KR); Sang Kyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/961,060

(22) Filed: Oct. 6, 2022

(65) Prior Publication Data

US 2023/0031107 A1 Feb. 2, 2023

Related U.S. Application Data

(63) Continuation of application No. 17/409,242, filed on Aug. 23, 2021.

(30) Foreign Application Priority Data

Jun. 14, 2021 (KR) ........................ 10-2021-0076852

(51) Int. Cl.
| | | |
|---|---|---|
| *A61B 5/0205* | (2006.01) | |
| *A61B 5/00* | (2006.01) | |
| *A61B 5/0245* | (2006.01) | |
| *A61B 5/026* | (2006.01) | |

(52) U.S. Cl.
CPC ........ *A61B 5/02055* (2013.01); *A61B 5/6831* (2013.01); *A61B 5/7246* (2013.01);
(Continued)

(58) Field of Classification Search
CPC ... A61B 5/7246; A61B 5/6831; A61B 5/0245; A61B 5/0261; A61B 5/681;
(Continued)

(56) References Cited

U.S. PATENT DOCUMENTS

| | | |
|---|---|---|
| 8,226,294 B2 | 7/2012 | Bieberich et al. |
| 9,939,334 B2 | 4/2018 | Yarden |

(Continued)

FOREIGN PATENT DOCUMENTS

| | | | |
|---|---|---|---|
| JP | 2018013395 A | * | 1/2018 |
| JP | 2018-21833 A | | 2/2018 |

(Continued)

*Primary Examiner* — May A Abouelela
*Assistant Examiner* — Anna Roberts
(74) *Attorney, Agent, or Firm* — Sughrue Mion, PLLC

(57) ABSTRACT

An apparatus for estimating a core body temperature of an object is provided. According to one embodiment, the apparatus includes a plurality of sensors configured to obtain data from an object and a processor configured to obtain a surface temperature, a heat flux, a skin blood flow rate, and a blood flow velocity by using the data obtained from the plurality of sensors, obtain a skin thermal conductivity based on the skin blood flow rate, and estimate a core body temperature of the object based on the surface temperature, the heat flux, the skin thermal conductivity, and the blood flow velocity of the object.

8 Claims, 11 Drawing Sheets

(52) U.S. Cl.
CPC ........... *A61B 5/0245* (2013.01); *A61B 5/0261* (2013.01); *A61B 2562/0271* (2013.01)

(58) Field of Classification Search
CPC .............. A61B 5/6898; A61B 5/02125; A61B 5/02416; A61B 5/318; A61B 5/01; A61B 5/28; A61B 5/6802; A61B 5/7275; A61B 2562/0271; A61B 2560/0223; A61B 5/02055

See application file for complete search history.

(56) References Cited

U.S. PATENT DOCUMENTS

| | | | |
|---|---|---|---|
| 10,088,373 B2 | 10/2018 | Durrer et al. | |
| 10,209,209 B2* | 2/2019 | Ikeda | A61B 5/6824 |
| 10,668,206 B2 | 6/2020 | Newell et al. | |
| 10,926,605 B2 | 2/2021 | Salter | |
| 10,959,942 B2 | 3/2021 | Sandvang et al. | |
| 2015/0313486 A1* | 11/2015 | Mestha | A61B 5/7225 600/301 |
| 2016/0213354 A1 | 7/2016 | Levin et al. | |
| 2018/0242850 A1 | 8/2018 | Ellis et al. | |
| 2019/0343397 A1 | 11/2019 | Meisal | |
| 2020/0132329 A1 | 4/2020 | Ito et al. | |
| 2021/0177272 A1 | 6/2021 | Seyama et al. | |

FOREIGN PATENT DOCUMENTS

| | | | |
|---|---|---|---|
| JP | 2018021833 A | * | 2/2018 |
| JP | 2019-211270 A | | 12/2019 |
| KR | 10-2021-0006073 A | | 1/2021 |
| WO | 2017/001701 A1 | | 1/2017 |

* cited by examiner

APPARATUS AND METHOD FOR ESTIMATING BODY TEMPERATURE

CROSS-REFERENCE TO RELATED APPLICATION(S)

This application is a continuation application of U.S. application Ser. No. 17/409,242, filed Aug. 23, 2021, which claims priority to Korean Patent Application No. 10-2021-0076852, filed on Jun. 14, 2021, in the Korean Intellectual Property Office, the entire disclosure of which is incorporated herein by reference for all purposes.

BACKGROUND

1 Field

The disclosure relates to an apparatus and a method for estimating a core body temperature using a plurality of sensors.

2. Description of Related Art

In general, body temperature is one of basic vital signs and has very important clinical significance. A body temperature sensor is applicable to various applications, such as detection of whether a patient is infected or whether there is a thermal side effect of a drug, detection or prediction of ovulation time, and the like. However, it is not easy to measure a core body temperature using a mobile device, such as a wearable device, because the skin temperature and the core body temperature may differ depending on the ambient temperature. General temperature sensors may include contact sensors and non-contact sensors. Contact sensors include sensors that detect changes in electrical resistance, such as resistance temperature detectors (RTDs) and thermistors, and thermocouples that detect electromotive force. In addition, non-contact sensors include thermopiles and microbolometers, which measure infrared rays emitted from the human body surface to measure a body temperature. A related art body temperature measurement technique is greatly affected by changes in external ambient temperature and environmental conditions that affect heat transfer, such as humidity, air flow, and the like.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, provided is an apparatus for estimating a body temperature, including: a plurality of sensors configured to obtain data from an object; and a processor configured to obtain a surface temperature, a heat flux, a skin blood flow rate, and a blood flow velocity of the object by using the data obtained from the plurality of sensors, obtain a skin thermal conductivity based on the skin blood flow rate, and estimate a core body temperature of the object based on the surface temperature, the heat flux, the skin thermal conductivity, and the blood flow velocity.

The processor may be further configured to estimate the core body temperature through a linear combination of a ratio between the heat flux and the skin thermal conductivity, the surface temperature, and the blood flow velocity.

The plurality of sensors may include a photoplethysmogram (PPG) sensor configured to emit light toward the object and measure a PPG signal by detecting light scattered or reflected from the object, and the processor may be further configured to obtain the skin blood flow rate based on the PPG signal measured by the PPG sensor.

The processor may be further configured to extract a feature from the PPG signal and obtain the skin blood flow rate from the extracted feature by using a model that defines a correlation between the feature and the skin blood flow rate.

The processor may be further configured to obtain the skin thermal conductivity based on the obtained skin blood flow rate by using at least one of a predefined linear relational expression or a non-linear relational expression.

The plurality of sensors may include a temperature sensor configured to measure the surface temperature of the object.

The plurality of sensors may include a plurality of temperature sensors or heat flow sensors and the processor may be further configured to obtain the heat flux based on data measured through the plurality of temperature sensors or heat flow sensors.

A first temperature sensor of the plurality of sensors may be provided on a contact surface of a thermal conducting material in contact with the object, a second temperature sensor of the plurality of sensors may be provided on an opposite side of the contact surface of the thermal conducting material, and the processor may be further configured to obtain the heat flux based on a temperature measured by the first temperature sensor, a temperature measured by the second temperature sensor, and a thermal conductivity of the thermal conducting material.

The plurality of sensors may include at least one of a PPG sensor or an electrocardiogram (ECG) sensor, and the processor may be further configured to obtain the blood flow velocity based on at least one of a PPG signal obtained through the PPG sensor or an ECG signal obtained through the ECG sensor.

The processor may be further configured to extract a first characteristic point from the PPG signal, extract a second characteristic point from the ECG signal, and obtain the blood flow velocity based on a time difference between the extracted first characteristic point and the extracted second characteristic point.

The processor may be further configured to obtain the blood flow velocity based on a difference between time points of a propagation wave component and a reflection wave component of the PPG signal.

According to an aspect of an example embodiment, provided is a method of estimating a body temperature, including: obtaining data from an object through a plurality of sensors; obtaining a surface temperature, a heat flux, a skin blood flow rate, and a blood flow velocity of the object by using the obtained data; obtaining a skin thermal conductivity based on the skin blood flow rate; and estimating a core body temperature of the object based on the surface temperature, the heat flux, the skin thermal conductivity, and the blood flow velocity.

The estimating of the core body temperature of the object may include estimating the core body temperature through a linear combination of a ratio between the heat flux and the skin thermal conductivity, the surface temperature, and the blood flow velocity.

The obtaining of the data may include emitting light toward the object by using a photoplethysmogram (PPG)

sensor and measuring a PPG signal by detecting light scattered or reflected from the object, and the obtaining of the skin blood flow rate of the object may include obtaining the skin blood flow rate based on the measured PPG signal.

The obtaining of the skin blood flow rate of the object may include extracting a feature from the PPG signal and obtaining the skin blood flow rate from the extracted feature by using a model that defines a correlation between the feature and the skin blood flow rate.

The obtaining of the heat flux of the object may include obtaining the heat flux based on data measured by using a plurality of temperature sensors or a plurality of heat flow sensors.

The obtaining of the data may include obtaining at least one of a PPG signal or an electrocardiogram (ECG) signal by using at least one of a PPG sensor or an ECG sensor, and the obtaining of the blood flow velocity may include obtaining the blood flow velocity based on at least one of the PPG signal or the ECG signal.

The obtaining of the blood flow velocity may include extracting a first characteristic point from the PPG signal, extracting a second characteristic point from the ECG signal, and measuring the blood flow velocity based on a time difference between the extracted first characteristic point and the extracted second characteristic point.

The obtaining of the blood flow velocity may include obtaining the blood flow velocity based on a difference between time points of a propagation wave component and a reflection wave component of the PPG signal.

According to an aspect of an example embodiment, provided is a wearable device including: a main body; a strap connected to both ends of the main body; a plurality of sensors provided on a surface of the main body and configured to, based on the main body being in contact with an object, obtain data the an object; and a processor configured to obtain a surface temperature, a heat flux, a skin blood flow rate, and a blood flow velocity of the object by using the data obtained from the plurality of sensors, obtain a skin thermal conductivity based on the skin blood flow rate, and estimate a core body temperature of an object based on the surface temperature, the heat flux, the skin thermal conductivity, and the blood flow velocity.

BRIEF DESCRIPTION OF THE DRAWINGS

The above and other aspects, features, and advantages of embodiments of the disclosure will be more apparent from the following description taken in conjunction with the accompanying drawings.

DETAILED DESCRIPTION

Figure 1:
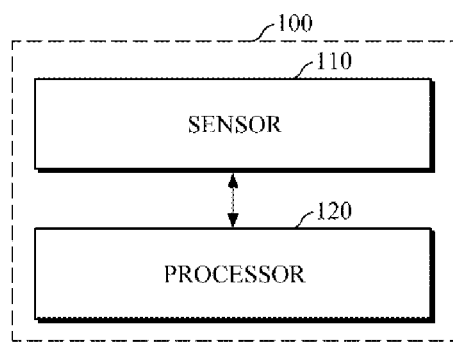
FIG. 1 is a block diagram of an apparatus for estimating body temperature according to an example embodiment.

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification. The relative size and depiction of the elements may be exaggerated for clarity, illustration, and convenience.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

FIG. 1 is a block diagram of an apparatus for estimating body temperature according to an example embodiment.

Referring to FIG. 1, an apparatus 100 for estimating body temperature may include a sensor 110 and a processor 120.

The sensor 110 may include a plurality of sensors configured to obtain data for estimating a core body temperature from an object, and the processor 120 may use the data obtained from the plurality of sensors to obtain a surface temperature, heat flux, and skin blood flow rate, skin thermal conductivity, and blood flow velocity of the object.

The sensor 110 may include a temperature sensor that measures a surface temperature upon contact of the object, and the processor 120 may obtain the surface temperature using the data obtained from the temperature sensor. For example, the sensor 110 may include a thermistor to measure the surface temperature of the object. The thermistor is a contact type temperature sensor for measuring the temperature of an object, and may be in contact with a portion (e.g., a wrist) of the object and measure the surface temperature of the portion of the object.

The sensor 110 may include a plurality of temperature sensors or heat flow sensors, and the processor 120 may obtain a heat flux based on data measured through the plurality of temperature sensors or heat flow sensors. The heat flow sensor is a sensor capable of measuring a heat flux through measurement of a heat flow density, and may be in contact with the object and measure the heat flux. The heat flow sensor may have a volume of 1×1×0.5 mm³ or less, but is not limited thereto.

Figure 2:
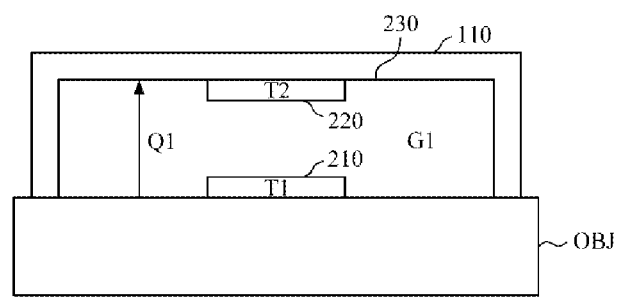
FIG. 2 is a diagram schematically illustrating a structure of a sensor for measuring a heat flux using a plurality of temperature sensors according to an example embodiment.

FIG. 2 is a diagram schematically illustrating a structure of the sensor 110 for measuring a heat flux using a plurality of temperature sensors according to an example embodiment.

Referring to FIG. 2, the sensor 110 may include a thermal conducting material 230, a first temperature sensor 210 disposed on a contact surface of the thermal conducting material 230 in contact with an object OBJ, and a second temperature sensor 220 disposed on the opposite side of the contact surface of the thermal conducting material 230 in contact with the object OBJ. The processor 120 may measure a heat flux Q1 based on a temperature T1 measured by the first temperature sensor 210, a temperature T2 measured by the second temperature sensor 220, and thermal conductivity G1 of the thermal conducting material 230, and the heat flux Q1 may be expressed as Equation 1.

$$Q1=(T1-T2)\times G1 \tag{1}$$

Here, T1 represents the surface temperature of an object OBJ measured by the first temperature sensor 210, and T2 represents the surface temperature of the thermal conducting material 230 measured by the second temperature sensor 220. The heat flux Q1 may be measured by multiplying a value obtained by subtracting the surface temperature T2 of the thermal conducting material 230 from the surface temperature T1 of the object OBJ by the thermal conductivity G1 of the thermal conducting material 230. The first and second temperature sensors 210 and 220 may have an area of 0.5×0.5 mm² or less, and the height of the thermal conducting material 230 may be 1 mm or less, but the disclosure is not limited thereto. In addition, the first and second temperature sensors may include a thermistor.

The sensor 110 may include a photoplethysmogram (PPG) sensor which emits light to an object and detects light scattered or reflected from the object to measure a PPG signal, and the processor 120 may obtain a skin blood flow rate based on the PPG signal measured by the PPG sensor.

For example, the processor 120 may extract a feature from the PPG signal and obtain the skin blood flow rate from the extracted feature using a model that defines a correlation between the feature and the skin blood flow rate.

Figure 3:
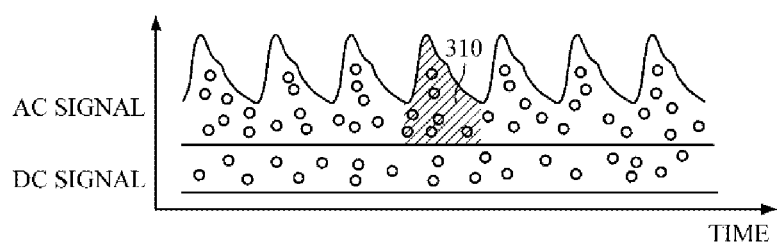
FIG. 3 is a graph for describing an example of estimating a blood flow rate from a feature of a photoplethysmogram (PPG) signal according to an example embodiment.

FIG. 3 is a graph for describing an example of estimating a blood flow rate from a feature of a PPG signal according to an example embodiment.

The PPG signal includes a direct current (DC) signal and an alternating current (AC) signal. The DC signal is an unchanging signal, which relates to bones and muscles, and the AC signal is a signal which changes depending on the inflow of blood ejected from the heart into arteries. Referring to FIG. 3, an upper portion corresponds to an AC signal that changes according to a pulse wave, and a lower portion corresponds to a DC signal that remains unchanged. The AC signal indirectly reflects the change in the blood flow rate because it can indicate whether the amount of incoming arterial blood is increasing or decreasing. Accordingly, the processor 120 may extract an area under curve (AUC), which is an area 310 of an AC component portion of the PPG signal, as a feature of the PPG signal, and estimate the blood flow rate using the extracted AUC. In this case, skin blood flow rate may be obtained from the extracted AUC using a blood flow estimation model which defines the correlation between the AUC and the skin blood flow rate in advance.

In another example, according to Equation 2, the processor 120 may obtain a perfusion index that indicates the ratio of the AC signal and the DC signal of the PPG signal as a feature of the PPG signal, and estimate the blood flow rate using the obtained perfusion index. For example, the skin blood flow rate may be obtained from the obtained perfusion index using a blood flow estimation model which defines the correlation between the perfusion index and the skin blood flow rate in advance.

$$PI(\text{Perfusion Index})=AC/DC \tag{2}$$

However, the disclosure is not limited thereto, and as other features of the PPG signal for estimation of blood flow rate, time related to a propagation wave component of the PPG signal, an amplitude corresponding to the time, time related to a reflection wave component of the PPG signal, and an amplitude corresponding to the time may be extracted as characteristic points. In this case, the characteristic points related to the propagation wave component and the reflection wave component may be extracted based on a secondary differential signal of the PPG signal. For example, a time position of the first local minimum point in the secondary differential signal may be extracted as time related to the propagation wave component, and time positions of the second and third local minimum points may each be extracted as time related to the reflection wave component. In addition, time and/or amplitude at a predetermined point in a designated interval of the PPG signal, for example, time and/or amplitude at an amplitude peak point, and time at an internally dividing point between time at an amplitude peak point and time related to the propagation wave component and/or amplitude corresponding to the time, may be extracted as characteristic points. Here, the internally dividing point may be an intermediate point between two time points or a point obtained by internally dividing a line between the two time points in a predetermined ratio.

The sensor 110 may include at least one of a PPG sensor or an electrocardiogram (ECG) sensor, and the processor 120 may measure a blood flow velocity based on at least one of a PPG signal obtained through the PPG sensor or an ECG signal obtained through the ECG sensor.

For example, when the PPG signal and the ECG signal are obtained from the PPG sensor and the ECG sensor, the processor 120 may extract a first characteristic point from the PPG signal and a second characteristic point from the ECG signal, and measure a blood flow velocity based on a time difference between the extracted first and second characteristic points.

Figure 4:
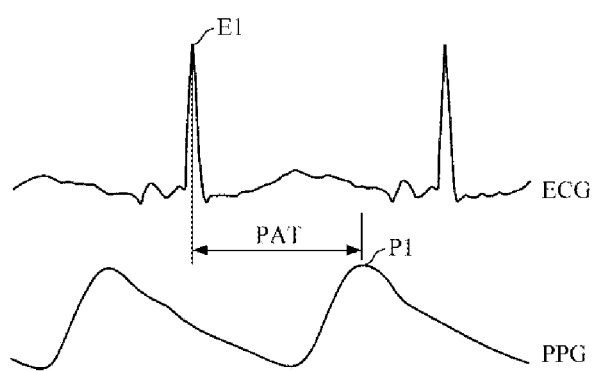
FIG. 4 is a diagram for describing a time difference measurement between a photoplethysmogram (PPG) signal and an electrocardiogram (ECG) signal for measuring a blood flow velocity according to an example embodiment.

FIG. 4 is a diagram for describing a time difference measurement between a PPG signal and an ECG signal for measuring a blood flow velocity according to an example embodiment.

For example, referring to FIG. 4, the processor 120 may extract a maximum point P1 of the PPG signal as a first characteristic point, and also extract, as a second characteristic point, an R wave E1 that is generated in the ECG signal immediately before the first characteristic point. The blood flow velocity may be measured using a pulse arrival time (PAT), which is a time difference between the extracted first characteristic point of the PPG signal and the extracted second characteristic point of the ECG signal.

In another example, when the plurality of sensors include only the PPG sensors and a PPG signal is received from the PPG sensor, the processor 120 may obtain at least two points of the PPG signal as characteristic points, and measure the blood flow velocity based on a time difference between the two obtained points.

Figure 5:
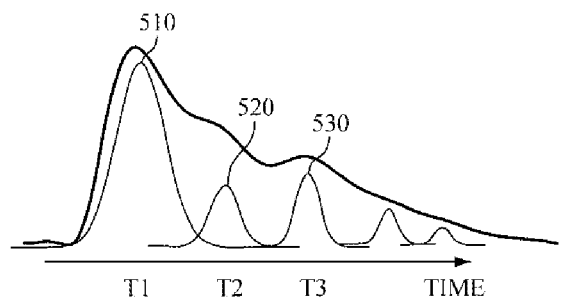
FIG. 5 is a diagram for describing a time difference measurement between a propagation wave component and a reflection wave component for measuring a blood flow velocity according to an example embodiment.

FIG. 5 is a diagram for describing a time difference measurement between a propagation wave component and a reflection wave component for measuring a blood flow velocity according to an example embodiment. Referring to FIG. 5, a time point T1 of a propagation wave component 510 constituting the PPG signal may be obtained as a first characteristic point, a time point T3 of a second reflection wave component 530 may be obtained as a second characteristic point, and a blood flow velocity may be measured based on a time difference (T3−T1) between the obtained first and second characteristic points. However, the first characteristic point and the second characteristic point are not limited thereto, and the time point T1 of the propagation wave component 510 and a time point T2 of a first reflection wave component 520 may be obtained as the first characteristic point and the second characteristic point, respectively, or the time point of the first reflection wave component 520 and the time point T3 of the second reflection wave component 530 may be obtained as the first characteristic point and the second characteristic point, respectively. In this case, the processor 120 may obtain a secondary differential signal of the PPG signal, and obtain the time points of the propagation wave component and the reflection wave components by using time of a local minimum point of the obtained secondary differential signal.

In another example, the processor 120 may measure the blood flow velocity based on the slope of the propagation wave component constituting the PPG signal. Generally, the larger the slope of the propagation wave component, the faster the blood flow velocity. The maximum value of the slope corresponding to the fastest blood flow velocity may be determined based on the slope at a point where the first differentiation of the propagation wave component becomes 0, or the slope between the foot and the peak of the propagation wave component.

In another example, the processor 120 may measure the blood flow velocity based on a pulse transit time (PTT), which is a time difference between PPG signals measured at different positions of the object. For example, a time point at the first peak point of a PPG signal measured at a first position of an object may be obtained as a first characteristic point, a time point at the first peak point of a PPG signal measured at a second position of the object may be obtained, and the blood flow velocity may be measured based on the time difference between the first characteristic point and the second characteristic point. However, this is merely an example, and various first and second characteristic points may be obtained.

The blood flow velocity thus obtained is generally associated with heat loss. In general, heat loss occurs during heat transfer from a deep portion to a wrist through arterial blood, so correction for the heat loss is required to accurately estimate a core body temperature. The heat loss may be expressed as Equation 3.

$$T_{loss} \propto D/V \propto T_{PAT} \quad (3)$$

Here, $T_{loss}$ denotes heat loss, D denotes a distance from a skin surface to a deep portion, V denotes blood flow velocity, and $T_{PAT}$ denotes pulse arrival time.

As such, the blood flow velocity V has an inverse relationship with the pulse arrival time $T_{PAT}$, the blood flow velocity may be estimated from the pulse arrival time obtained through this relationship, and the heat loss at the time when the core body temperature is estimated may be compensated for based on the obtained blood flow velocity.

The processor 120 may obtain skin thermal conductivity based on the obtained skin blood flow rate using at least one of a predefined linear relational expression or a predefined non-linear relational expression. For example, the skin thermal conductivity may be expressed as Equation 4.

$$G = k + \alpha Fs \quad (4)$$

Here, G denotes skin thermal conductivity, Fs denotes skin blood flow rate, and k and α denote predetermined values. It can be seen that the skin thermal conductivity G has a linear relationship with the skin blood flow rate Fs.

The processor 120 may estimate the core body temperature of the subject based on the obtained surface temperature, heat flux, skin thermal conductivity, and blood flow velocity, and may be expressed as Equation 5.

$$T_{body} = T_{skin} + Qs/(k + \alpha Fs) + \beta V \quad (5)$$

Here, $T_{body}$ denotes core body temperature, $T_{skin}$ denotes skin surface temperature, Qs denotes heat flux, Fs denotes skin blood flow rate, (k+αFs) denotes thermal conductivity, V denotes blood flow velocity, α and β are predetermined values, and the processor 120 may estimate core body temperature through a linear combination of the ratio between the heat flux and the thermal conductivity, the surface temperature, and the blood flow velocity.

Figure 6:
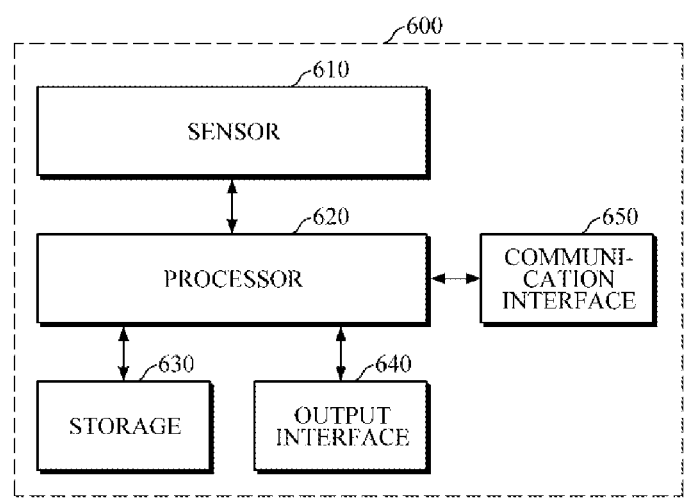
FIG. 6 is a block diagram of an apparatus for estimating body temperature according to another example embodiment.

FIG. 6 is a block diagram of an apparatus for estimating body temperature according to another example embodiment.

Referring to FIG. 6, an apparatus 600 for estimating body temperature may include a sensor 610, a processor 620, a storage 630, an output interface 640, and a communication interface 650. In this case, configurations of the sensor 610 and the processor 620 may be the same as those of the sensor 110 and the processor 120 of the embodiment of FIG. 1, and thus detailed descriptions thereof will not be reiterated.

The storage 630 may store information associated with core body temperature estimation. For example, data (e.g., spectra) obtained through a plurality of sensors 610 and a processing result of the processor 620, for example, surface temperature, heat flux, skin blood flow rate, skin thermal conductivity, or blood flow velocity of an object, may be stored.

The storage 630 may include a storage medium, such as a memory of flash memory type, hard disk type, multimedia card micro type, or card type (e.g., SD or XD memory), random access memory (RAM), static random access memory (SRAM), read-only memory (ROM), electrically erasable programmable read-only memory (EEPROM), programmable read-only memory (PROM), magnetic memory, magnetic disk, optical disk, or the like, but is not limited thereto.

The output interface 640 may provide the processing result of the processor 620 to a user. For example, the output interface 640 may display an estimated body temperature value of the processor 620 on a display. In this case, when the estimated body temperature value is outside a normal range, warning information may be provided to the user by adjusting the color or the thickness of a line for the user's easy recognition or by displaying along with the normal range. In addition, the output interface 640 may provide the estimated core body temperature value to the user through an audio output module, such as a speaker or the like, or a haptic module, together with or independently of a visual display, in a non-visual manner, such as voice, vibration, tactile sensation, or the like.

The communication interface 650 may transmit and receive various data associated with core body temperature estimation by communicating with an external device. The external device may include an information processing device, such as a smartphone, a tablet PC, a desktop PC, a notebook PC, or the like. For example, a body temperature estimation result may be transmitted to an external device, such as a user's smartphone, so that the user may manage and monitor a component analysis result through the device having a relatively superior performance.

The communication interface 650 may communicate with the external device by using various wired or wireless communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) communication, Ultra-Wideband (UWB) communication, Ant+ communication, Wi-Fi Direct (WFD) communication, Radio Frequency Identification (RFID) communication, third generation (3G) communication, fourth generation (4G) communication, fifth generation (5G) communication, and the like. However, this is merely an example and is not intended to be limiting.

Figure 7:
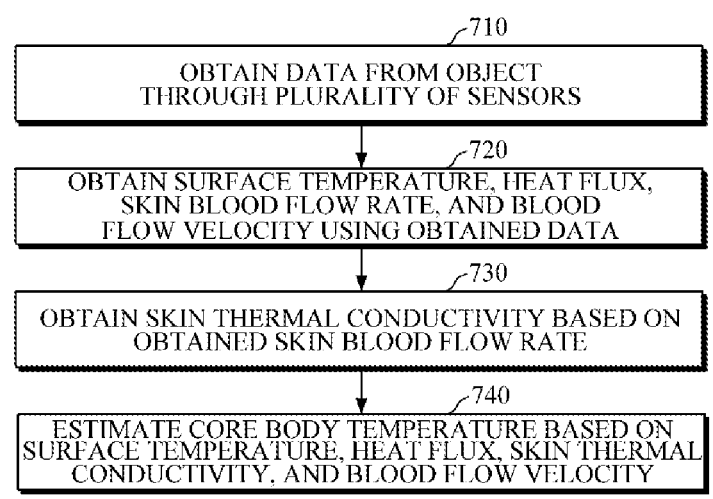
FIG. 7 is a flowchart illustrating a method of estimating body temperature according to an example embodiment.

FIG. 7 is a flowchart illustrating a method of estimating body temperature according to an example embodiment.

The method of FIG. 7 is an example embodiment of a method of estimating body temperature performed by the apparatuses 100 and 600 for estimating body temperature according to the embodiments of FIGS. 1 and 6. Hereinafter, the method will be described in brief to avoid redundancy.

Referring to FIG. 7, the apparatus for estimating body temperature may obtain data from an object through a plurality of sensors in 710. In this case, the plurality of sensors may include a temperature sensor, a heat flow sensor, a PPG sensor, an ECG sensor, and the like to obtain a parameter necessary for estimating a core body temperature.

Then, a surface temperature, heat flux, a skin blood flow rate, and a blood flow velocity may be obtained using the obtained data in 720.

In this case, the surface temperature of the object may be obtained using data obtained from the temperature sensor.

In addition, the heat flux may be obtained using data measured using a plurality of temperature sensors or heat flow sensors.

In addition, light may be emitted to the object by using the PPG sensor, a PPG signal may be measured by detecting light scattered or reflected from the object, and the skin blood flow rate may be obtained based on the measured PPG signal. For example, a feature may be extracted from the PPG signal, and the skin blood flow rate may be obtained from the feature extracted using a model that defines the correlation between the feature and the skin blood flow rate.

Also, pulse transit time may be obtained using at least one of the PPG sensor or the ECG sensor, and the blood flow velocity may be obtained using the obtained pulse transit time. For example, at least one of a PPG signal or an ECG signal may be obtained, and a pulse transit time may be obtained based on at least one of the obtained PPG signal and ECG signal. For example, a first characteristic point may be extracted from the PPG signal, a second characteristic point may be extracted from the ECG signal, and pulse transit velocity may be obtained based on a time difference between the extracted first and second characteristic points, or a difference between time points of a propagation wave component and a reflection wave component of the PPG signal.

Then, skin thermal conductivity may be obtained based on the obtained skin blood flow rate in 730.

Then, a core body temperature of the object may be estimated based on the surface temperature, heat flux, skin thermal conductivity, and blood flow velocity of the object in 740. For example, the core body temperature may be estimated through a linear combination of the ratio between the heat flux and the obtained thermal conductivity, the surface temperature, and the blood flow velocity.

FIGS. 8 to 11 are diagrams illustrating examples of a structure of an electronic device including the apparatus 100 or 600 for estimating body temperature.

Figure 8:
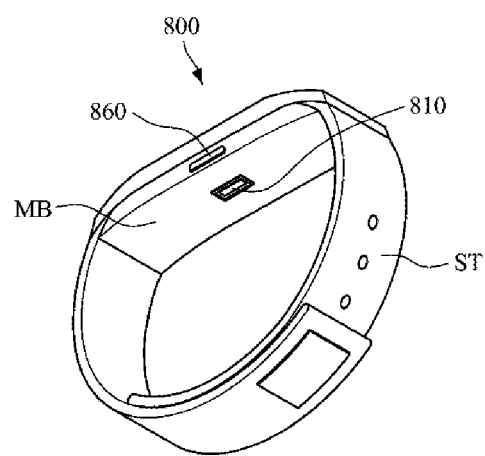
FIGS. 8 to 11 are diagrams illustrating examples of a structure of an electronic device including an apparatus for estimating body temperature according to example embodiments.

Referring to FIG. 8, an electronic device may be implemented as a smart watch type wearable device, and may include a main body MB and a wrist strap ST.

The main body MB may have various types of structures. A battery may be embedded in the main body MB and/or the strap ST to supply power to various modules. The strap ST may be connected to both ends of the main body MB, enabling the main body MB to be worn on a user's wrist, and may be flexible so as to be bent around the user's wrist. The strap ST may include a first strap and a second strap separate from each other. One ends of the first strap and the second strap may be connected to each end of the main body MB and the first strap and the second strap may be fastened to each other using fastening means (e.g., a fastener) provided on the other sides thereof. In this case, the fastening means may be provided as Velcro fastening, pin fastening, or the like, but is not limited thereto. In addition, the strap ST may be provided as one integrated piece, such as a band, which is not separated into pieces.

Various modules are included in the main body MB. A sensor 810, a processor, an output interface, a storage, and a communication interface may be mounted in the main body MB. However, in an example embodiment, at least one of the display, the storage, and the communication interface may be omitted according to the size and shape of form factor.

The sensor 810 may include a plurality of sensors including an optical sensor or a temperature sensor, and may be disposed on a rear surface of the main body MB so as to obtain data for measuring a core body temperature from the wrist by being in contact with an upper portion of the user's wrist when the main body MB is worn on the user's wrist.

A manipulator 860 may be provided on a side of the main body MB as illustrated. The manipulator 860 may receive a user's command and transmit the command to the processor. The manipulator 860 may include a power button for turning on/off the wearable device 800.

The processor mounted in the main body MB may be electrically connected to various modules including the sensor 810. The processor may obtain surface temperature, heat flux, skin blood flow rate, and blood flow velocity using the data obtained from a plurality of sensors 810, obtain skin thermal conductivity based on the skin blood flow rate, and estimate core body temperature of the object based on the skin surface, heat flux, skin thermal conductivity, and blood flow velocity of the object. For example, the processor may estimate the core body temperature through a linear combination of the ratio between the obtained heat flux and thermal conductivity, the surface temperature, and the blood flow velocity.

A display may be provided on a front surface of the main body MB, and various application screens containing temperature information, time information, received message information, and the like may be displayed thereon. For example, an estimated core body temperature value may be displayed on the display. In this case, when the estimated body temperature value is outside a normal range, warning information may be provided to the user by adjusting the color or the thickness of a line for the user's easy recognition or by displaying along with the normal range.

Figure 9:
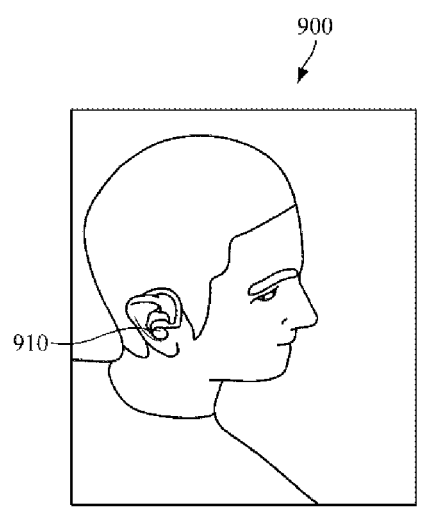

Referring to FIG. 9, the electronic device may also be implemented as an ear-wearable device, as illustrated in a diagram 900.

The ear wearable device may include a main body and an ear strap. The user may wear the electronic device by wearing the ear strap on the auricle. The ear strap may be omitted depending on the shape of the ear-wearable device. The main body may be inserted into the external auditory meatus of the user. A sensor 910 may be mounted in the main body. The ear-wearable device may acoustically provide an estimation result of body temperature to the user, or may transmit the estimation result to an external device, for example, a mobile device, a tablet device, a PC, etc. through a communication module provided in the main body.

Figure 10:
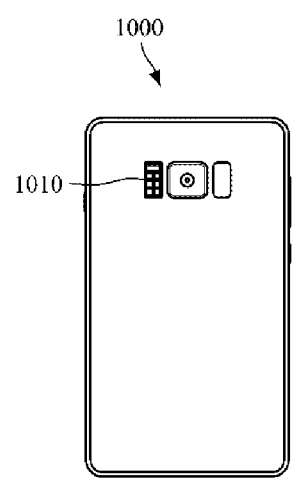

Referring to FIG. 10, the electronic device may be implemented as a mobile device 1000, such as a smartphone.

The mobile device 1000 may include a housing and a display panel. The housing may form the outer appearance of the mobile device 1000. The display panel and cover glass may be sequentially arranged on a first surface of the main body, and the display panel may be exposed to the outside through the cover glass. A sensor 1010, a camera module, and/or an infrared sensor may be disposed on a second surface of the housing.

In one embodiment, a sensor unit configured to measure an optical signal from a user's finger may be disposed on the rear surface of a main body of the smartphone 1000, and a second sensor unit, a temperature sensor, or the like may be disposed on a fingerprint sensor on the main body, a side power button, or a volume button, or at a separate position on the front and rear surface of the main body to estimate the core body temperature.

In addition, when the user requests estimation of body temperature by executing an application installed in the mobile device 1000, data may be obtained using the sensor 1010, the core body temperature may be estimated using a processor in the mobile device, and the estimated value may be provided to the user as an image and/or sound.

Figure 11:
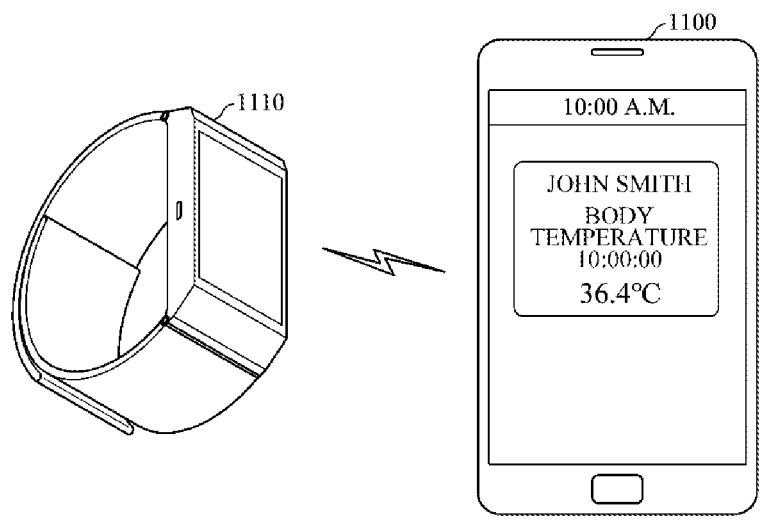

Referring to FIG. 11, the electronic device may be implemented by a combination of a watch-type wearable device and a smartphone. However, this is merely one example, and a combination of various electronic devices is possible. For example, a processor configured to estimate core body temperature may be mounted in a main body 1100 of a smartphone. Upon receiving a request for estimating body temperature, the processor of the smartphone may communicate with a communication interface mounted in a main body 1110 of a wearable device through a communication interface of the smartphone to control the wearable device to obtain data, such as an optical signal, skin surface temperature, etc. In addition, upon receiving the data, such as an optical signal, skin surface temperature, etc. from the wearable device, the processor may estimate core body temperature and output the result on a display of the smartphone through an output interface as illustrated.

The example embodiments may be implemented as computer readable codes in a computer readable record medium. Codes and code segments of the computer program may be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A smart watch comprising:
    a main body;
    a strap connected to the main body;
    a plurality of sensors configured to obtain data from an object based on the main body being in contact with the object, the plurality of sensors comprising:
        a first temperature sensor disposed on a first surface of a thermal conducting material, and configured to measure a first temperature; and
        a second temperature sensor disposed on a second surface of the thermal conducting material, and configured to measure a second temperature;
    a memory storing one or more instructions; and
    at least one processor, which while the strap is wrapped around a wrist such that the main body is worn on the wrist, is configured to execute the one or more instructions:
        obtain a skin surface temperature based on the first temperature;

obtain a skin thermal conductivity and a blood flow velocity based on signals obtained from at least one of the plurality of sensors;

obtain a heat flux based on a difference between the first temperature and the second temperature and a thermal conductivity of the thermal conducting material; and estimate a core body temperature of the object through a linear combination of a ratio between the heat flux and the skin thermal conductivity, the skin surface temperature, and the blood flow velocity, wherein the thermal conducting material has a height in a range of 0.4 mm to 1 mm, wherein the linear combination of the ratio between the heat flux and the skin thermal conductivity, the skin surface temperature, and the blood flow velocity is a sum of the ratio between the heat flux and the skin thermal conductivity, the skin surface temperature, and a weighted value of the blood flow velocity.

2. The smart watch of claim 1, wherein the plurality of sensors further comprise a photoplethysmogram (PPG) sensor configured to emit light toward the object and measure a PPG signal by detecting light scattered or reflected from the object, and wherein the at least one processor is further configured to obtain a skin blood flow rate based on the PPG signal, and obtain the skin thermal conductivity based on the skin blood flow rate.

3. The smart watch of claim 1, wherein the at least one processor is further configured to obtain the skin thermal conductivity by obtaining a skin blood flow rate based on the data obtained from the plurality of sensor and by applying at least one of a predefined linear relational expression or a non-linear relational expression to the skin blood flow rate.

4. A method of estimating a body temperature, the method comprising:
obtaining data from an object through a plurality of sensors that comprise a first temperature sensor disposed on a first surface of a thermal conducting material and configured to measure a first temperature, and a second temperature sensor disposed on a second surface of the thermal conducting material and configured to obtain a second temperature;

obtaining a skin surface temperature based on the first temperature;

obtaining a skin thermal conductivity and a blood flow velocity based on signals obtained from at least one of the plurality of sensors;

obtaining a heat flux based on a difference between the first temperature and the second temperature and a thermal conductivity of the thermal conducting material; and estimating a core body temperature of the object through a linear combination of a ratio between the heat flux and the skin thermal conductivity, the skin surface temperature, and the blood flow velocity, wherein the thermal conducting material has a height in a range of 0.4 mm to 1 mm, and wherein the linear combination of the ratio between the heat flux and the skin thermal conductivity, the skin surface temperature, and the blood flow velocity is a sum of the ratio between the heat flux and the skin thermal conductivity, the skin surface temperature, and a weighted value of the blood flow velocity.

5. The method of claim 4, wherein the obtaining of the data comprises emitting light toward the object by using a photoplethysmogram (PPG) sensor and measuring a PPG signal by detecting light scattered or reflected from the object, wherein the method further comprises obtaining a skin blood flow rate of the object based on the PPG signal, and wherein the obtaining the skin thermal conductivity comprises obtaining the skin thermal conductivity based on the skin blood flow rate.

6. The method of claim 4, wherein obtaining the skin thermal conductivity comprises:
obtaining a skin blood flow rate of the object based on the data obtained through the plurality of sensors; and
obtaining the skin thermal conductivity by applying at least one of a predefined linear relational expression or a non-linear relational expression to the skin blood flow rate.

7. An electronic device comprising:
a memory configured to store one or more instructions;
a communication interface configured to receive data measured by a plurality of sensors that comprise a first temperature sensor disposed on a first surface of a thermal conducting material and configured to measure a first temperature, and a second temperature sensor disposed on a second surface of the thermal conducting material and configured to measure a second temperature; and
at least one processor configured to execute the one or more instructions to:
obtain a skin surface temperature based on the first temperature;
obtain a skin thermal conductivity and a blood flow velocity based on signals obtained from the plurality of sensors;
obtain a heat flux based on a difference between the first temperature and the second temperature and a thermal conductivity of the thermal conducting material; and
estimate a core body temperature of an object through a linear combination of a ratio between the heat flux and the skin thermal conductivity, the skin surface temperature, and the blood flow velocity,
wherein the linear combination of the ratio between the heat flux and the skin thermal conductivity, the skin surface temperature, and the blood flow velocity is a sum of the ratio between the heat flux and the skin thermal conductivity, the skin surface temperature, and a weighted value of the blood flow velocity.

8. An electronic device comprising:
a first temperature sensor configured to measure a skin temperature of an object when the first temperature sensor is in contact with the object;
a second temperature sensor configured to measure an internal temperature of the electronic device while the first temperature sensor is measuring the skin temperature of the object;
a photoplethysmogram (PPG) sensor configured to emit a light toward the object and measure a PPG signal based on the light scattered or reflected from the object;
an electrocardiogram (ECG) sensor configured to measure an ECG signal while at least one electrode of the ECG sensor is in contact with the object;
a memory configured to store one or more instructions; and
at least one processor configured to execute the one or more instructions to:

obtain a skin thermal conductivity and a blood flow velocity based on the PPG signal and the ECG signal;

obtain a heat flux based on a difference between the internal temperature and the skin temperature and a thermal conductivity of a thermal conducting material provided between the first temperature sensor and the second temperature sensor; and estimate a core body temperature of the object through a linear combination of a ratio between the heat flux and the skin thermal conductivity, the skin surface temperature, and the blood flow velocity, wherein the linear combination of the ratio between the heat flux and the skin thermal conductivity, the skin surface temperature, and the blood flow velocity is a sum of the ratio between the heat flux and the skin thermal conductivity, the skin surface temperature, and a weighted value of the blood flow velocity.

* * * * *